Jan. 12, 1971 D. L. ARMSTRONG Plant Pat. 3,016
ROSE PLANT
Filed Jan. 10, 1969
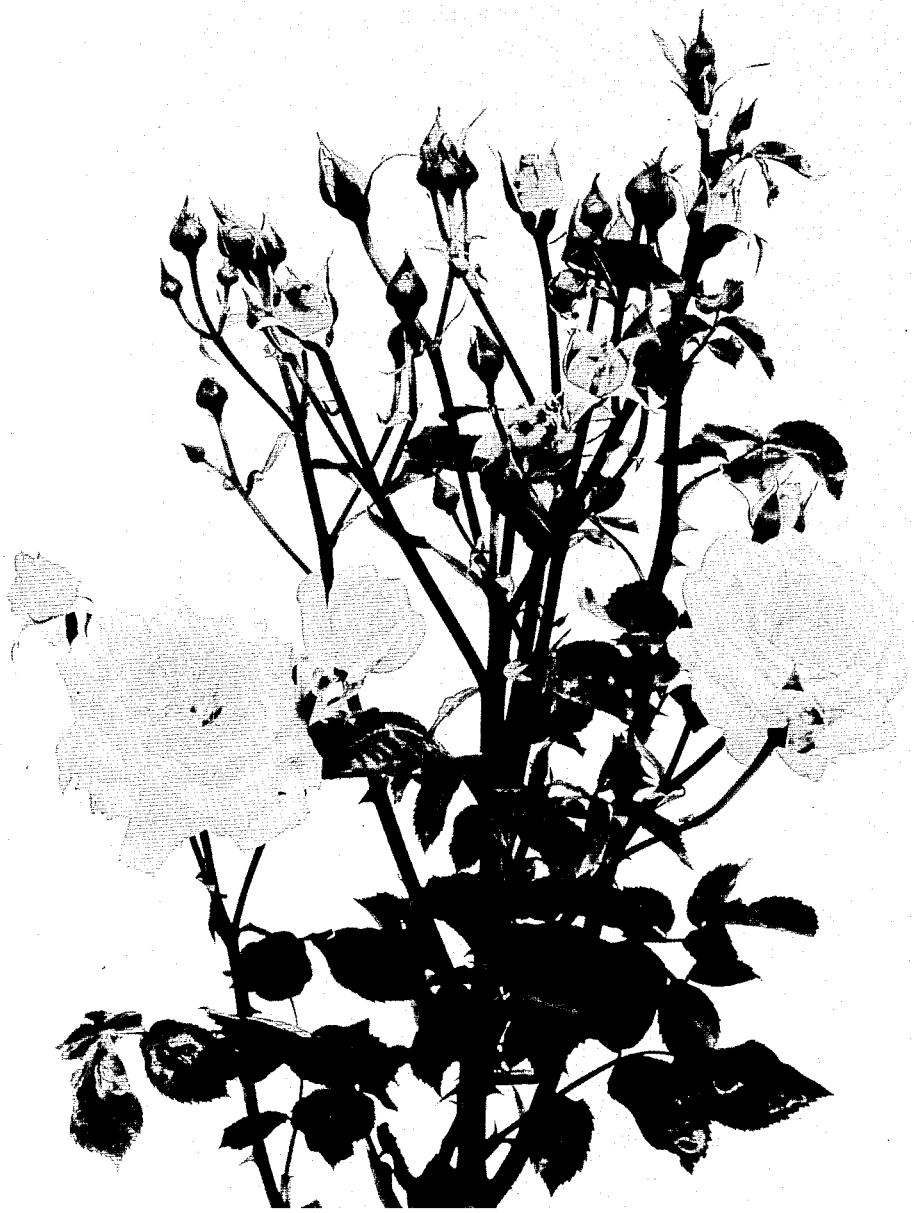

United States Patent Office

Plant Pat. 3,016
Patented Jan. 12, 1971

3,016
ROSE PLANT

David L. Armstrong, Upland, Calif., assignor to Armstrong Nurseries, Inc., Ontario, Calif., a corporation of California Filed Jan. 10, 1969, Ser. No. 790,488
Int. Cl. A01h 5/00
U.S. Cl. Plt.—22 1 Claim

ABSTRACT OF THE DISCLOSURE

A rose plant of the floribunda class which is moderately low growing, and has semi-glossy leaves of leathery texture comprising three to seven leaflets of moderate size; the flowers of said plant having a moderate fragrance and being unusually formal in the arrangement of their double petals, most of which are precisely-imbricated, delicately-waved and fluted, said flowers tending to deepen to a vermilion-orange color early in the flower life, thereafter paling to an unusual brick-orange color; the peduncles having a number of stipitate glands sufficiently pigmented to render them easily visible to the eye; the plant bearing its flowers sometimes on a single stem but usually in clusters of five or more, the clusters being carried upon strong stems of medium to long length; said plant further having a tendency to set hips rather freely under garden conditions, such as prevail in Ontario, Calif.

This invention relates to a new variety of rose plant of the floribunda class. The plant is moderately low growing in its habit, and is particularly adapted for outdoor cultivation, and for casual cut flowers. The plant was bred by crossing Heat Wave (Plant Pat. No. 1,786) as the seed parent and Spartan (Plant Pat. No. 1,357) as the pollen parent, and holds its distinguishing characteristics through succeeding propagations by budding. It was propagated in Ontario, Calif.

The plant is distinguished from its seed parent, Heat Wave, in the following respects, either severally or in combination:

The new variety of the present invention has a moderately vigorous growth, whereas the plant of the Heat Wave rose is very vigorous. Furthermore, the foliage of this new variety may be composed of as many as seven leaflets, whereas the foliage of Heat Wave rarely comprises more than five leaflets. Whereas the new variety frequently produces ten to fifteen seeds per hip, Heat Wave characteristically provides only five to eight seeds per hip. Insofar as the flower is concerned, the overall coloration of the mature bloom may be described as brick-orange, in contrast to Heat Wave, which manifests an intense orange-scarlet color. Furthermore, the flowers of the new variety are from half an inch to an inch smaller than those of Heat Wave, although the petals of the new variety are much more numerous, ranging from forty to seventy, together with six to ten petaloids, in comparison with a petal count of twenty-six to thirty-six in the seed parent.

The new variety is distinguished from its pollen parent, Spartan, in the following ways:

The new variety is characteristically moderate in growth and relatively low growing, in contrast to Spartan, which is very vigorous and has a tall habit of growth. The foliage of the new variety extends generally horizontally in its position on the canes, whereas the foliage of Spartan characteristically droops. The new variety sets seed quite readily, by natural means, whereas the Spartan plant sets very little seed under normal garden conditions. Insofar as the flower is concerned, the new variety manifests only slight to moderate fragrance, whereas the flowers of Spartan are very fragrant. The mature flower of the new variety is brick-orange, the color being quite distinct from that of the Spartan flowers, which latter may be described as salmon-orange to reddish coral in color. As was the case with reference to the seed parent, the petalage of the new variety is heavier than with Spartan, which normally carries only about thirty petals.

The accompanying drawing illustrates the plant in color, and shows the flowering thereof, from bud to full bloom.

The flowers of the new variety, as observed in Ontario, Calif., are sometimes borne on single stems, but more usually are found in clusters of five or more to the stem, the clusters being regular in form and the stems which carry them being strong and of medium to long length. The blooms are abundant in normal outdoor growth, and are almost continuous during the growing season. The fragrance varies from slight to moderate.

Bud: As to the bud: The peduncle is of average length and of average caliper, being erect and usually smooth with a few to several stipitate glands and none, or only a few, small prickles. Its color lies between Ocher Red (Pl. XXVII Ridgway) and Walnut Brown (Pl. XXVIII Ridgway). Before the calyx breaks the buds are small, short, and ovoid in form. As the calyx breaks, the color displayed lies between Delft Rose (p. 108, Pl. 020 Wilson) and Blood Red (p. 166, Pl. 820/1 Wilson). The inner surfaces of the sepals have a fine wooly tomentum, appearing on the margins of alternate sepals. The margins of other sepals carry several to many stipitate glands and small slender foliaceous parts. The outer surfaces of the sepals usually have several to many small stipitate glands. As the first petal opens, it is usually small and short in size, and ovoid or sometimes urn-shaped in form. Its color on the outside lies between Vermilion (p. 18, Pl. 18/1 Wilson) and Scarlet (p. 19, Pl. 19/1 Wilson), with a small area at the base of the petal which is near Uranium Green in color (p. 63, Pl. 63/3 Wilson). The inner surface of the first petal is between Mandarin Red (p. 17, Pl. 17/1 Wilson) and Vermilion (p. 18, Pl. 18/1 Wilson) and the small area at the base of the petal is close to Primrose Yellow (p. 65, Pl. 601/2 Wilson). The bud opens up well. Its opening is not retarded or prevented by variations in the weather, either cold, hot, wet or dry.

Bloom: The blooms, when fully open, may range from small to average size, namely from about 3" to about 3½" in diameter. The petalage is double and ranges from forty to seventy petals, plus six to ten petaloids irregularly arranged. The bloom is high-centered at first and may maintain this form or become slightly cupped. The petals at first are tightly cupped.

Later, at maturity, they become more loosely cupped. The tips of the petals are rolled outwardly.

Petals: The petals are of medium thickness and have a moderately leathery texture. They are satiny to velvety as to their inner surfaces, while their outer surfaces are satiny. The outer petals are broadly obovate in form with flat apex. They sometimes have one or two notches. The intermediate petals are between round and broadly obovate in form, rounded at the apex. The inside petals have a form which is intermediate between round and obovate, with apex likewise rounded. The petal colors may be modified by being shaded and/or washed with other colors.

The following description is of the newly opened flower of a rose grown outdoors in the month of April, in Ontario, Calif.:

The outer surface of the outside petal is between Scarlet (p. 19, Pl. 19/2 Wilson) and Germanium Lake (p. 20, Pl. 20/2 Wilson). The inside surface of the petal is between Scarlet (p. 19, Pl. 19/1 Wilson) and Geranium Lake (p. 20, Pl. 20/1 Wilson). The small area at the base is near Primrose Yellow (p. 65, Pl. 601/3 Wilson), both inside and outside the outer petals. The outer surface of the intermediate petals is between Vermilion (p. 18, Pl. 18/2 Wilson) and Scarlet (p. 19, Pl. 19/2 Wilson), and the small area at the base of the petal, both on the inner and outer surface is near Primrose Yellow (p. 65, Pl. 601/3 Wilson). The inside surface is close to Vermilion (p. 18, Pl. 18/2 Wilson). The outer surface of the inner petals lies between Vermilion (p. 18, Pl. 18/1 Wilson) and Scarlet (p. 19, Pl. 19/2 Wilson). As with the intermediate petals, the small area at the base, both on the inner surface and on the outer surface of the inner petals is near Primrose Yellow (p. 65, Pl. 601/3 Wilson). The inner surface of the inner petals is near Vermilion (p. 18, Pl. 18/1 Wilson).

The following description is of a flower of the new variety that had been open for three days in the month of April in Ontario, Calif.:

The color of the outside surface of the outer petals was between Geranium Lake (p. 20, Pl. 20/2 Wilson) and Carmine (p. 21, Pl. 21/2 Wilson). The small area at the base, both on the inner and outer surface of the outside petal was near Uranium Green (p. 63, Pl. 63/3 Wilson). The inside surface of the outer petals was between Scarlet (p. 19, Pl. 19/2 Wilson) and Geranium Lake (p. 20, Pl. 20/2 Wilson). The color of both the inside and outside surfaces of the inner petals conformed closely to that of the outer petals except that a very small area near the base of the petal was more nearly Dresden Yellow (p. 64, Pl. 64/3 Wilson). The general color effect of the newly opened flower was between Vermilion (p. 18, Pl. 18/1 Wilson) and Scarlet (p. 19, Pl. 19/1 Wilson). After the bloom had been open for three days, the general color effect lay between Scarlet (p. 19, Pl. 19/1 Wilson) and Geranium Lake (p. 20, Pl. 20/2 Wilson).

The flowers drop off cleanly. They are not particularly affected by cold, hot, wet or dry weather. They persist, on the bush in the garden, for three or four days in the month of April. Cut roses grown outdoors, and kept at livingroom temperatures in the month of April, will also last for three or four days.

REPRODUCTIVE ORGANS

Stamens: The stamens are of average number, arranged regularly about the pistils, a few being mixed with petaloids.

Filaments: The filaments are short, being 4 to 8 mm. in length, and are of a nearly Crimson color (p. 22, Pl. 22/2 Wilson). Most of them carry anthers.

Anthers: The anthers are small and all open approximately at once. Both on the upper and lower side, the margins are near Saffron Yellow (p. 7, Pl. 7/2 Wilson), the remainder being closer to Maize Yellow (p. 69, Pl. 607/3 Wilson).

Pollen: The pollen is sparse to moderate and near Indian Yellow in color (p. 6, Pl. 6/1 Wilson).

Pistils: The pistils also are average in number, there being approximately sixty of them.

Styles: The styles are uneven, short to average length, thin and bunched. The upper third of the style is near Rose Madder (p. 23, Pl. 23 Wilson), the remainder being near Primrose Yellow (p. 65, Pl. 601/3 Wilson).

Stigma: The stigma is near Rose Opal (p. 110, Pl. 022/3 Wilson).

Ovaries: Usually all of the ovaries are enclosed in the calyx.

Hips: The hips are short to average length, and between ovoid and globular in shape. As they begin to mature they are near Absinthe Green (Pl. XXXI Ridgway) and are smooth, with thick fleshy walls.

Sepals: The sepals fall soon.

Seeds: The seeds are of medium size and range from ten to fifteen in number.

PLANT

Foliage: The leaves are compound, usually having three to seven leaflets. They are normal to abundant in number, are of medium size, leathery and semi-glossy in texture. The leaflets are oval in shape with acute apex and round base. The margin is simply serrate. On the upper surface, the mature leaf is between Forest Green (Pl. XVII Ridgway) and Empire Green (Pl. XXXII Ridgway). The under surface of the mature leaf is near Light Elm Green in color (Pl. XVII Ridgway). The young leaves, on their upper surfaces, are near Light Cress Green (Pl. XXXI Ridgway) whereas the undersurface is near Asphodel Green (Pl. XLI Ridgway) with areas overlaid by a color approaching Prussian Red (Pl. XXVII Ridgway).

Rachis: The rachis is of average size, its upper side being grooved and carrying several stipitate glands on the edges. The underside is smooth with a few stipitate glands and a few small prickles.

Stipules: The stipules are of medium length, narrow to medium width, with short points turning out at an angle of more than 45°.

Growth: The plant has a bushy upright and spreading habit of growth, being much branched. The growth is moderate, and the canes are of medium caliper. The main stems are near Light Elm Green (Pl. XVII Ridgway) in color, and carry many medium long, almost straight, large prickles which are medium long and narrow at the base. They are near Walnut Brown (Pl. XXVIII Ridgway). The small prickles are few to several in number, and their color lies near Walnut Brown (Pl. XXVIII Ridgway). There are no hairs on the stems. The branches are near Bice Green (Pl. XVII Ridgway), and several large prickles carried by these branches are of medium length, almost straight, with medium long narrow base. The color approximates Roods Brown (Pl. XXVIII Ridgway). The small prickles, few in number, are of the same color as the large ones. There are no hairs on the branches.

New shoots: The new shoots are near Citrine Drab (Pl. XL Ridgway), but are overlaid, on the side which is exposed to the sun, with a color near Sorghum Brown (Pl. XXXIX Ridgway). There are several large prickles on the new shoots and these are of medium length, hooked slightly downward, with medium long narrow bases. They are near Ocher Red in color (Pl. XXVII Ridgway). There are a few small prickles on the new shoots, and these have the same color as the large prickles. There are no hairs on the new shoots.

The plant has a better-than-average resistance to mildew, at least as compared to other commercially available varieties raised under comparable conditions in Ontario, Calif.

I claim:

1. A rose plant of the floribunda class, substantially as shown and described, which is moderately low growing, and has semi-glossy leaves of leathery texture comprising three to seven leaflets of moderate size; the flowers of said plant having a moderate fragrance and being unusually formal in the arrangement of their double petals, most of which are precisely-imbricated, delicately-waved and fluted, said flowers tending to deepen to a vermilion-orange color early in the flower life, thereafter paling to an unusual brick-orange color; the peduncles having a number of stipitate glands sufficiently pigmented to render them easily visible to the eye; the plant bearing its flowers sometimes on a single stem but usually in clusters of five or more, the clusters being carried upon strong stems of medium to long length; said plant further having a tendency to set hips rather freely under garden conditions, such as prevail in Ontario, Calif.

No references cited.

ROBERT E. BAGWILL, Primary Examiner